United States Patent [19]
Reierson

[11] Patent Number: 6,136,221
[45] Date of Patent: Oct. 24, 2000

[54] PHOSPHATION REAGENT

[75] Inventor: Robert Lee Reierson, Cranbury, N.J.

[73] Assignee: Rhodia Inc., Cranbury, N.J.

[21] Appl. No.: 09/232,974

[22] Filed: Jan. 21, 1999

Related U.S. Application Data

[63] Continuation of application No. 08/677,179, Jul. 9, 1996, abandoned, which is a continuation of application No. 08/399,253, Mar. 6, 1995, Pat. No. 5,554,781, which is a continuation-in-part of application No. 08/220,069, Mar. 30, 1994, abandoned.

[51] Int. Cl.$^7$ .................................................. C01B 25/24
[52] U.S. Cl. ...................... 252/183.14; 423/304; 423/316
[58] Field of Search .......................................... 252/183.14

[56] References Cited

U.S. PATENT DOCUMENTS

| | | | |
|---|---|---|---|
| 3,235,627 | 2/1966 | Mansfield | 260/926 |
| 3,686,371 | 8/1972 | Hasegawa | 260/980 |
| 4,126,650 | 11/1978 | Via et al. | 260/980 |
| 4,139,485 | 2/1979 | Imokawa et al. | 252/135 |
| 4,350,645 | 9/1982 | Kurosaki et al. | 260/978 |
| 4,436,748 | 3/1984 | Ong et al. | 424/275 |
| 4,670,575 | 6/1987 | Kurosaki et al. | 558/146 |
| 4,874,883 | 10/1989 | Uphues et al. | 558/150 |
| 5,254,691 | 10/1993 | Mori et al. | 548/111 |
| 5,342,845 | 8/1994 | Chokai et al. | 514/305 |

FOREIGN PATENT DOCUMENTS

| | | |
|---|---|---|
| 4114416 | 8/1966 | Japan . |
| 426730 | 3/1967 | Japan . |
| 4326492 | 11/1968 | Japan . |
| 3188089 | 8/1991 | Japan . |

OTHER PUBLICATIONS

Research Disclosure, vol. 354, p. 671 (1993).
G. Imokawa, J. Am. Oil Chem.Soc., 55,839 (1978).
G. Imokawa, J. Am. Oil Chem.Soc., 56,604 (1979).
A. Nelson & A. Toy, Inorg. Chem., 2,775 (1963).
T. Kurosaki et al., Oil Chemistry, 39 (4), 259 (1990).
T. Glonek, et al, J. Am.Chem.Soc., 92, 7214 (1970).
T. Glonek, et al, Inorg. Chem., 13, 2337 (1974).
T. Glonek, et al, Phosphorus 1975, 157.
T. Glonek, et al. J. Am. Chem. Soc., 97, 206 (1975).
T. Glonek, et al, Phosphorus and Sulfur 3, 137 (1977).
M. Watanabe, et al, Mem. Chubu Inst. Tech., 81 (1983).
T. Kurosaki, et al, Comun.Jorn.Com.Esp.Deterg., 19, 191 (1988).
T. Khwaja, et al, J. Chem. Soc. (C) 1970, 2092.
T. Kurosaki, et al, Oil Chemistry, 39 (4), 250 (1990).

*Primary Examiner*—Michael G. Ambrose
*Attorney, Agent, or Firm*—John A. Shedden

[57] ABSTRACT

The invention relates to a process for producing a unique phosphation reagent and to a simple, single-stage process utilizing is reagent to produce alkyl phosphate esters having high monoalkyl phosphate content in combination with low dialkyl phosphate, trialkyl phosphate, phosphoric acid and residual alcohol.

3 Claims, 1 Drawing Sheet

FIG. 1

PHOSPHATION REAGENT

This is a continuation of U.S. Ser. No. 08/677,179 filed Jul. 9, 1996 now abandoned; which was a continuation of U.S. Ser. No. 08/399,253 filed Mar. 6, 1995 now U.S. Pat. No. 5,554,781; which was a continuation-in-part of U.S. Ser. No. 08/220,069 filed Mar. 30, 1994 now abandoned.

FIELD OF THE INVENTION

This invention relates to a unique phosphating agent and to a simple, reliable process utilizing this agent to produce phosphate ester compositions which have high monoalkyl phosphate content in combination with low dialkyl phosphate, trialkyl phosphate, phosphoric acid and residual alcohol.

DESCRIPTION OF THE PRIOR ART

The superior performance of fatty alcohol based anionic phosphate esters enriched in monoalkyl ester content relative to dialkyl content has been demonstrated, particularly with respect to surfactant esters used in cosmetic and personal hygiene cleansers. These high monoalkyl phosphate surfactants exhibit a unique combination of good detergency and low skin irritancy, especially in comparison to alkyl sulfate or alkyl sulfonate surfactants (G. Imokawa, et al., U.S. Pat. No. 4,139,485, Feb. 13, 1979; G. Inokawa, J. Am. Oil Chem. Soc. 56, 604 (1979)). In a given alkyl phosphate mixture, other important properties such as water miscibility, Krafft point and foam production also are a function of the relative amounts of monoalkyl and dialkyl phosphate. As the dialkyl phosphate content increases, the solubility, foaming ability, and detergency decrease and the Krafft point increases. The desirable range for a "monoalkyl" phosphate composition has been defined to be wherein the ratio of monoalkyl to dialkyl phosphate is at least 80:20 weight percent (U.S. Pat. No. 4,139,485). Acceptable performance was found at 70:30, and relatively little additional improvement was obtained above 90:10.

Typical phosphation processes do not produce product mixtures with the high monoalkyl phosphate together with the low dialkyl phosphate, low phosphoric acid and low residual alcohol contents necessary to obtain the above advantages. The two commonly used phosphating agents produce two extremes in the compositional range.

In one case, polyphosphoric acid, commercially available as 115% phosphoric acid (also described as 83 weight percent phosphoric anhydride, $P_4O_{10}$) reacts with alcohols to produce a mixture of high monoalkyl phosphate and low dialkyl phosphate but also high phosphoric acid. This is expected since the polyphosphoric acid consists essentially of linear chains varying from one to more than fifteen phosphorus atoms connected by oxygen anhydride linkages. Although the alcoholysis reaction is complex because it involves many intermediates of differing chain lengths and even cyclic structures, ultimately one molecule of phosphoric acid would theoretically be produced from the "tail-end" of each chain or alternatively, the amount of phosphorus remaining as $H_3PO_4$ would be equal to 1/n wherein n equals the average polymer chain length (F. Clarke and J. Lyons, J. Am. Chem. Soc. 88, 4401, (1966)).

On this premise, the amount of phosphoric acid which would be produced from the chain ends by complete alcoholysis of a sample of an approximately 117% polyphosphoric acid was calculated to be 23.2 mole percent. Reaction of simple alcohols with an equimolar amount of 117% polyphosphoric acid was reported to produce from 21.0 to 23.8% orthophosphoric acid (F. Clarke and J. Lyons, op. cit.). An excess of alcohol was necessary to drive the reaction to completion. Similarly, reaction of an excess of lauryl alcohol with 115% polyphosphoric acid at 70–83° C. for 15 hours, then to 94° C. for four hours, produced a very viscous oil which solidified upon standing, (m.p. about 80° C.), with no residual pyrophosphates and an orthophosphate composition of 23 mole percent phosphoric acid, 73% monolauryl phosphate and 4% dilauryl phosphate. Expressed as weight percent of total phosphorus products, this would be 9.6% phosphoric acid, 83.0% monolauryl phosphate and 7.4% dilauryl phosphate, to note how the numbers are changed by the molecular weight differences.

To produce a monoalkyl phosphate without dialkyl phosphate contamination theoretically could be done from pyrophosphoric acid (A. Nelson and A. Toy, Inorg. Chem., 2, 775, (1963)). Alcoholysis would yield one mole of phosphoric acid and one mole of monoalkyl phosphate (also F. Clarke and J. Lyons, op. cit.).

Reaction of lauryl alcohol in a molar amount equal to the pyrophosphoric acid plus tripolyphosphoric acid in 105% polyphosphoric acid at room temperature to 65° C. over a two hour period followed by fourteen hours at 71–72° C. produced a creamy, very viscous mass which contained about 69 mole % phosphoric acid, 20 mole % monolauryl phosphate and 11% pyrophosphate intermediates. Addition of excess alcohol to the mass at room temperature followed by heating to 52° C. over three hours to complete the conversion of the pyrophosphates gave a solution in which the molar ratios were 76% phosphoric acid, almost 24% monolauryl phosphate, and only a trace of dilauryl phosphate. The theoretical distribution based on the original 105% polyphosphoric acid composition was 73% phosphoric acid and 27% lauryl phosphate.

Because of the relatively low reactivity of the pyrophosphate intermediates with the alcohols, an excess of one of the reactants is usually used. U.S. Pat. No. 3,235,627 discloses that an equivalent ratio of 1.2–4.0 polyphosphoric acid per mole alcohol produces a mixture of 85–100% monoalkyl phosphates. In this patent, the optimum ratio per mole alcohol is 1.0 to 1.3 moles polyphosphoric acid, expressed as 82–84% (by weight) $P_2O_5$ (or $P_4O_{10}$; also equivalent to about 115% weight percent polyphosphoric acid). This '627 patent notes however that a large percentage of unreacted alcohol will remain, i.e. incomplete phosphation will occur, if an excess of this polyphosphoric acid is not used. For instance, an equivalent amount (0.5 "mole" expressed as $P_2O_5$ or 0.25 $P_4O_{10}$ per mole alcohol) produced only a 56% conversion; hence 44% residual alcohol. This patent provides references to the art which practice the use of excess alcohol, claiming that undesirable dialkyl phosphates are produced. Additionally, T. Kurosaki et al., Comun. Jorn. Com. Esp. Deterg. 19, 191 (1988) states that monoalkyl phosphate can be formed with little formation of dialkyl phosphate, but also that polyphosphoric acid was required in excess to complete the reaction. In the graphical representation of his data, FIG. 14, p. 204, which covers the range of 100 to 115% polyphosphoric acid, he shows that the most concentrated acid evaluated, about 113%, produces only 60% alcohol conversion and requires a two-fold molar excess to achieve about 95% conversion. He concludes that in order to manufacture high purity monoalkyl phosphate, the removal of the resulting excess phosphoric acid coproduct from the mixture is required.

It is clear that the "polyphosphoric acid" reagents used by this reference were of lower effective equivalent polyphosphoric acid weight percent than that of the reagents of the instant invention which have a minimum of 118 weight percent.

A more recent, comprehensive study of alcohol phosphation by ortho- and polyphosphoric acids similarly shows the limitations of this approach, but considering the value of the high monoalkyl phosphate compositions, commercial processes have been developed based upon 115% polyphosphoric acid alone as the phosphation reagent (T. Kurosaki et al. *Oil Chemistry*, 39(4),259, (1990)).

The large amount of phosphoric acid thus unavoidably produced in processes based on the common, approximately 115% polyphosphoric acids, is an undesirable coproduct which is particularly troublesome in cosmetic products, electrolyte solutions, emulsions and in the spinning of synthetic fibers. Purification methods have therefore necessarily been developed to partition the acid and the organophosphate into layers which can then be separated (K. Aimono et al. Japan Kokai Tokyo Koho JP 03,188,089, Aug. 16, 1991; T. Kurosaki et al., U.S. Pat. No. 4,670,575, Jun. 2, 1987; G. Uphues et al. U.S. Pat. No. 4,874,883, Oct. 17, 1989)).

The other extreme of the product composition is produced by the use of phosphoric anhydride, $P_4O_{10}$. In contrast to 115% polyphosphoric acid, a viscous liquid, $P_4O_{10}$ is a white powder which is highly reactive with alcohols even at room temperature. It is a powerful dehydrating agent and relatively insoluble in most common organic solvents except those with which it reacts. If in excess or not adequately dispersed in the reaction liquor, it forms undesirable by-products, e.g. i) trialkyl phosphates from the primary alcohol and its dialkyl phosphate by dehydration and/or ii) darkly colored products resulting from the charring of the alcohol that was absorbed into the slowly dissolving, large chunks formed by agglomeration of the powder. Under favorable conditions of good mixing and cooling with precise control of adventitious moisture and reactant ratios, the reaction of $P_4O_{10}$ with alcohols still proceeds through a complex series of intermediates. Possible structures for these condensed phosphates have been prepared and characterized (T. Glonek et al., *J. Am. Chem. Soc.* 92, 7214 (1970); *Inorg. Chem.* 13, 2337 (1974); *Phosphorus* 1975, 157; *J. Am. Chem. Soc.* 97, 206 (1975); and *Phosphorus and Sulfur* 3, 137 (1977)). A theoretical sequence is outlined in FIG. 1. The problems with any attempt to control selectivity arise from the fact that each polyphosphate intermediate has its characteristic solubility and reaction rate. Branched phosphates, with three P—O—P bonds to the central phosphorus, are considerably more reactive than linear ones having two P—O—P bonds. The simple pyrophosphate, having only one P—O—P bond, is the least reactive polyphosphate. In addition, hydrolysis studies of the simple acids have shown that the acyclic tetra- and tripolyphosphates are more reactive than their monocyclic precursors, (M. Watanabe et al., *Mem. Chubu Inst. Tech.*, 81 (1983)).

In the presence of other hydroxy functional species such as adventitious water or a mixture of alcohols, the product distribution is a function of the concentration, (which is related to solubility), and the competitive reaction rates of each phosphate intermediate with each hydroxy compound. These conditions change throughout the course of the reaction as the more reactive species are preferentially consumed and their relative concentrations decrease.

Figure 1:
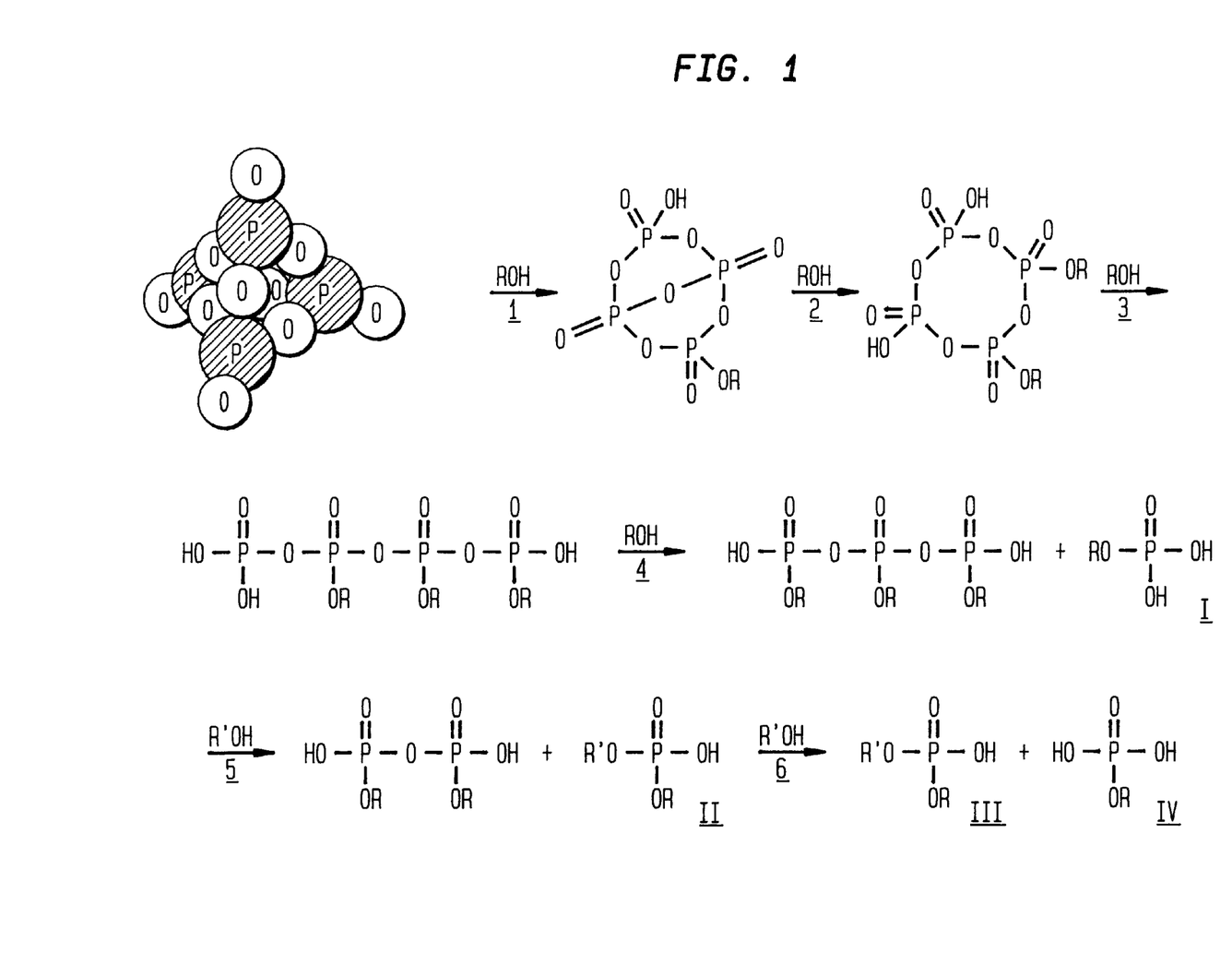
FIG. 1 describes the theoretical step-wise reaction of an alcohol with phosphoric anhydride ($P_4O_{10}$).

The sequence in FIG. 1 predicts that an equimolar mixture of monoalkyl phosphate (MAP) and dialkyl phosphate (DAP) would be formed under ideal conditions and, in fact, reaction of $P_4O_{10}$ with a two fold stoichiometric excess of lauryl alcohol, i.e. 12 moles per $P_4O_{10}$, under standard laboratory conditions produced a mixture of phosphates in a molar ratio of about 0.509 MAP:0.485 DAP:0.007 $H_3PO_4$.

A third option, which is the direct esterification of phosphoric acid, is not practical because of its low reactivity, and the difficulty realized in removing water from the polar and increasingly viscous product mixture. The high temperatures of at least 120° C., reduced pressure of 300 torr or less, preferably less than 50 torr, and/or the use of azeotropic solvents which are used to drive the reaction to completion also produce the undesirable dialkyl phosphates and still leave undesirable levels of unreacted phosphoric acid (T. Kurosaki, et al., *Oil Chemistry* 39(4)259, (1990)). Combination of an orthophosphoric acid with an alcohol under less than anhydrous conditions (specifically as 85% orthophosphoric acid) without less than atmospheric pressure, an azeotropic agent or temperatures considerably above the 100° C. water boiling point would not result in an esterification reaction. Similar product compositions may be obtained more conveniently by use of the aforedescribed use of polyphosphoric acid or phosphoric anhydride.

Several attempts to reduce the tendency of phosphoric anhydride to produce dialkyl phosphate coproduct have been reported. Early work postulated that in the optimum case, substitution of two moles of water for two of the six moles of alcohol required to completely convert $P_4O_{10}$ to orthophosphates would produce essentially four moles of the monoalkyl phosphate. (Sanyo Kasei Kogyo K. K., Japanese Patent Publication 41-14416 (1966)). As mentioned above, the reaction sequence is complex. Although high monoalkyl to dialkyl molar ratios of up to 94:6 were reported, substantial conversion of phosphoric anhydride to phosphoric acid also occurred, 60 mole percent, in this example, at the upper end of the "suitable range" of water content, and generally, excessively high levels of phosphoric acid throughout the series. The unreacted alcohol content was not reported, but under the stated conditions of stoichiometry, it could be presumed to be equal to the moles of phosphoric acid minus the moles of dialkyl phosphate or about 58 mole percent. The author clearly stated that the addition of water to the phosphoric anhydride followed by reaction with the alcohol was an unsuitable alternative.

Almost simultaneously, another case (Daiichi Kogyz Seiyaku Co., Ltd., Japanese Patent Publication 42-6730 (1967)) reported the similar use of 85% phosphoric acid (0.960 mole water per mole $H_3PO_4$). This strategy, however, was to react the orthophosphoric acid and the phosphoric anhydride separately with the alcohol apparently in the presence of the water introduced with the 85% phosphoric acid. The details are limited, but duplication of the examples clearly showed that the 85% phosphoric acid did not react with the alcohol under the stated conditions. Complete analysis of the reaction mixtures during and at the completion of the experimental sequence farther revealed that the conversion was not complete at the end of the stated reaction period, but rather was finished in the subsequent, apparently necessary work up procedures for separation and characterization of the monoalkyl ester product. Other products were not quantified. The quantities of monoalkyl phosphate found upon duplication of the examples in the laboratory were significantly lower than the high yields of monoalkyl phosphate reported.

A more recent study more precisely determined the affect of the ratios between water, alcohol and phosphoric anhydride on the phosphate product composition, again with particular emphasis upon the monoalkyl and dialkyl phosphate ratio (T. Kurosaki, et al. *Comun. Jorn. Com. Esp. Deterg.* 19, 191 (1988)). High resolution phosphorus-31 nuclear magnetic resonance spectroscopy was used to quantify the phosphorus species during the later stages of the reaction, after the phosphoric anhydride had all dissolved, and in the final mixtures.

The 85% and 105% phosphoric acids (separated into their percent "water" and "$P_4O_{10}$" content for calculation purposes) were also evaluated. The 105% acid, the lowest concentration of phosphoric acid which is free of residual water (i.e. anhydrous), was found to generally produce less favorable results than the use of water as a diluent in the acid or alone. Even under what appeared to be the most favorable ratios and method, the residual phosphoric acid content was still over 15 mole percent of the total phosphorus species and the monoalkyl phosphate leveled off at about 60 mole percent. The residual alcohol level was not reported.

The use of phosphorus oxychloride is not a good option because it is not selective; it produces three moles of hydrogen chloride per mole of phosphate, which is highly corrosive and must be scrubbed from the reactor emissions to prevent environmental pollution; and it produces an undesirable alkyl chloride by-product (T. Kurosaki et al., U.S. Pat. No. 4,350,645, Sep. 21, 1982).

Even within the limitations of the above phosphation agents, it is possible to obtain desirable intermediate product mixtures by judicious combinations of selected phosphation agents, alcohol and water in staged reaction sequences. For example, the addition of one mole of $P_4O_{10}$ to four moles of an unsaturated alcohol followed by a digestion period, then addition of two moles water and continued heating to completion was reported to yield a high monoalkyl phosphate containing a polymerizable vinyl group for applications in which the presence of any dialkyl phosphate would promote crosslinking of the polymer, and thus be very detrimental (T. Hasegawa, U.S. Pat. No. 3,686,371, Aug. 22, 1972).

A more complicated example involves preparation of a phosphate ester mixture by a standard reaction sequence, and then use of the resulting mixture as the reaction medium to which additional phosphoric anhydride, alcohol, and water are added. The intent is to produce the symmetrical dialkyl pyrophosphate as the major product, then to hydrolyze it to the monoalkyl phosphate in the final step (F. Via et al., U.S. Pat. No. 4,126,650, Nov. 21, 1978).

The best results were obtained by multiply staging the reagent addition and heel production events. That is, to the initially formed heel, the remaining phosphoric anhydride and alcohol are alternately added in four equal aliquots at the reaction temperature of 75–90° C. The mixture is then digested at 85° C. for two hours; water and 30% hydrogen peroxide added; and the reaction completed at 80° C. to yield a final product containing over 80 weight % monoalkyl acid phosphate (based on analysis by titration; phosphorus-31 nuclear magnetic resonance spectroscopy is now more accurate and precise).

The primary study (T. Kurosaki et al., U.S. Pat. No. 4,350,645, Sep. 21, 1982) also utilized a two stage process but in direct opposition to the above two examples. The '371 process, in fact, is the same as the Method 2 reported to be inferior by this principal author in his 1988 publication (vide supra).

The purpose of the first stage in '645 is to combine an equimolar mixture of water and alcohol with phosphoric anhydride (two moles each, per mole of $P_4O_{10}$) to prepare an intermediate composition, i.e. a heel. This monoalkyl pyrophosphate heel is then reacted with the remaining two $2\ ROH + 2H_2O + P_4O_{10} \longrightarrow$ moles of alcohol to convert the pyrophosphate intermediates to orthophosphates. The best product ratios realized for lauryl phosphate, about 0.821:0.081:0.099 MAP:DAP:$H_3PO_4$ (molar) and 0.829:0.134:0.037 (weight) (MAP:DAP weight ratio, 86.1:13.9) for this simplified two step process are comparable to the multiply staged addition process, considering the accuracy of the titrimetric analysis, (U.S. Pat. No. 4,126,650) and are superior to the extant single stage processes. Further specific evidence was provided by Comparative Example 1 in this case. The lauryl alcohol phosphation by 85% phosphoric acid and $P_4O_{10}$ is essentially the same as the Example 1 in 42-6730. This more completely defined composition, however, is reported as 66.2 mole % monoalkyl phosphate, 18.9% dialkyl phosphate and 14.9% phosphoric acid in contrast to the "yield of dodecyl monophosphate: 94.7%" reported in 42-6730.

The above summary essentially describes the state of the existing technology for the preparation of enriched monoalkyl phosphate compositions by direct phosphation and the desirable properties of these compositions, especially for mixtures with MAP:DAP weight ratios of 80:20 or greater. Other, even more sophisticated methods are known which involve the preparation of intermediates in multiple-step processes which have blocking groups that must be removed after the intermediates are used to phosphate the alcohol substrate. The more selective blocking groups would be derived from phenol, substituted phenols, catechol, or substituted triazoles (H. Mori et al., U.S. Pat. No. 5,254,691, Oct. 19, 1993; T. Khwaja et al. *J. Chem. Soc.* (C) 1970, 2092; and the references cited therein). However, these processes are too expensive to be viable for most commercial product applications.

SUMMARY OF THE INVENTION

The present invention relates to the discovery of a unique phosphating agent which can be used to produce in a single step, solventless process, phosphate ester compositions wherein the weight ratio of monoalkyl acid phosphate to dialkyl acid phosphate is greater than 80:20, concomitant with low levels of free phosphoric acid and residual alcohol.

The optimum phosphation reagent composition is from about 121–123%, expressed as an effective equivalent percent of polyphosphoric acid. The reagent is prepared by the intimate blending and exclusively reacting phosphoric anhydride ($P_4O_{10}$) with phosphoric acid ($H_3PO_4$) to produce a uniform slurry or paste.

The phosphate esters are formed by contacting the reagent paste or slurry with the organic alcohol (ROH) with sufficient stirring and temperature control to dissolve the reagent in the alcohol and carry the reaction to completion.

The primary phosphate ester products of the present invention have the general formula:

wherein R is as defined herein.

DETAILED DESCRIPTION OF THE INVENTION

A new process has been discovered which produces enriched monoalkyl phosphate compositions in a single step which avoids the disadvantages associated with the processes of the prior art. A unique phosphating agent is utilized which is a direct derivative of phosphoric anhydride in which phosphoric acid is used as a blocking group. The new agent may be prepared quantitatively under a wide range of times and temperatures and is stable to storage under anhydrous conditions. It dissolves more readily than phosphoric anhydride, is pumpable when warmed to reduce its viscosity, and can be added more rapidly to the alcohol without the highly exothermic heat of reaction problems characteristic of phosphoric anhydride. In contrast to the use of the commercially available 115–117% polyphosphoric acids, it is not necessary to use an excess of this phosphation reagent relative to the alcohol in order to achieve good conversion rates and low residual alcohol content. In fact, stoichiometrically equal amounts of alcohol and the phosphating reagent are most desirable. The phosphoric acid used as the blocking group is consumed in the process, hence does not contribute excessively to the residual amount. Consequently, the residual phosphoric acid concentration is comparable to that obtained by the most preferable, multi-staged processes previously described.

With the process of the instant invention, in which monoalkyl to dialkyl phosphate weight ratios greater than 80:20 are achieved, the weight percents of the residual alcohol and phosphoric acid are individually each less than 6%.

The action of this reagent is postulated to be as follows, for the simplest case of orthophosphoric acid as the blocking group.

These initial reactions are similar to those already shown in the theoretical $P_4O_{10}$ reactions with alcohol in FIG. 1 in which the R group would represent $H_2PO_3$—. The same principles apply but with important limitations.

The above series of reactions could continue, particularly if sufficient phosphoric acid were available, or by further reaction of the —OH functionalities on the blocking phosphate groups, until the more reactive branched phosphates ultimately have been converted to linear P—O—P structures. A very complex mixture of intermediates is likely formed. It is, therefore, important to limit the amount of phosphoric acid to a molar ratio of two per $P_4O_{10}$ molecule (or two phosphorus equivalents of phosphoric acid to the four phosphorus equivalents in $P_4O_{10}$). Substantially more phosphoric acid would convert the reactive branched intermediates to components of simple polyphosphoric acid, and substantially less would allow an undesirably high level of the highly reactive tetrahedral $P_4O_{10}$ and its first reaction product, the bicyclic phosphate, to remain. In essence, the latter two highly reactive phosphate species are converted to more controllably reactive intermediates, of which B and C are proposed as examples, and the relatively unreactive (under simple alcohol phosphation conditions) phosphoric acid is converted to more reactive polyphosphate intermediates.

Since the phosphorus-oxygen-phosphorus anhydride bonds being broken are being compensated by formation of new phosphorus-oxygen-phosphorus bonds, the energy released in these transformations is primarily that from opening the strained $P_4O_{10}$ and structure A polycyclic rings. These reactive intermediates are also converted in a stable, inorganic, phosphoric acid medium. Importantly, there are no organic compounds present, hence no opportunity for their $P_4O_{10}$ induced decomposition products to be produced.

This new phosphation reagent, represented empirically, but not exclusively as structures B and C, is in the form of a suspension of small, "fluffy", white particles in a viscous, clear matrix. It is stirrable above room temperature and therefore pumpable. It dissolves much more readily than $P_4O_{10}$, even though the particle size is much larger, and does not produce the hard, slowly soluble, black chunks which are encountered when $P_4O_{10}$ itself is mixed into a polyethoxylated alcohol. Since much of the ring strain energy has been released, the heat of reaction is primarily that resulting from conversion of the phosphorus-oxygen-phosphorus anhydride bonds to the carbon- oxygen-phosphorus ester and the hydrogen-oxygen-phosphorus acid bonds. This staged release of energy is much easier to control on a commercial process scale and the better control allows minimization of undesirable by-products.

The sequence of reactant addition to the reaction is not critical. For example, the alcohol can be added to the reactor containing the phosphation reagent or the phosphation reagent can be added directly to the alcohol. As is well known in the art, addition of alcohol to $P_4O_{10}$ powder can result in a vigorous, potentially uncontrollable and hazardous reaction.

Because of the transient nature of the initially formed phosphation reagent intermediates and the heterogenous nature of the sample, characterization is very difficult (T. Kurosaki et al., *Oil Chemistry* 39 (4), 250 (1990)). The branched (trisubstituted) phosphorus centers, even in the non-bicyclic intermediates, would be expected to be of such reactivity that some might be converted to linear, disubstituted species by reaction with terminal —$OPO_3H_2$ groups in the process of dissolving the sample in an inert solvent for analysis. However, an indication of the nature of this unique phosphation reagent is given by its phosphorus —31 nuclear magnetic resonance spectrum. For comparison, the principal component in 105 weight % polyphosphoric acid is phosphoric acid itself, 50 mole %, followed by pyrophosphoric acid, 40 mole %, and finally tripolyphosphoric acid, 10 mole % (including the end groups in the pyrophosphoric acid region). The spectrum for 115 weight % polyphosphoric acid still shows some orthophosphoric acid, 8 mole % at −0.5 ppm (relative to external 85% phosphoric acid); a more complex pattern at −13 to −14 ppm comprised of pyrophosphoric acid and the phosphates at the ends of the higher molecular weight chains, accounting for 46 mole % of the phosphorus species; and a similar pattern at −26 to −29 ppm, for the remaining 46 mole % internal chain phosphate groups. The spectrum of the novel reagent of this invention, in contrast, for a composition equivalent to 122.5 weight % phosphoric acid, shows only a trace of orthophosphoric acid; 11 mole % chain end and pyrophosphoric acid groups, at −13 to −14 ppm (only one P—O—P anhydride bond on the phosphorus); 87% internal chain and/or cyclic phosphate groups at −26 to −29 ppm (two P—O—P anhydride bonds on the phosphorus); and a small amount, 2 mole %, of branched phosphate groups (three P—O—P anhydride bonds on each phosphorus), at −37 to −39 ppm. Exhaustive interpretation would be difficult because of the wide range of possible structures. However, it is clear that signals characteristic of $P_4O_{10}$ (−60 ppm) and phosphoric acid are essentially absent, signals for branched and pyrophosphates are minimal, and the bulk of the phosphorus species are of the most desired cyclic or linear anhydride type.

The above comments and idealized reaction schemes are the inventor's attempt to theoretically explain the unusual and unexpected characteristics and properties of the reagents of this invention and are not meant to limit his discovery; the metes and bounds of which are determined by the scope of the claims.

The process by which the phosphation reagent may be prepared is by contacting and exclusively reacting phosphoric anhydride ($P_4O_{10}$) with phosphoric acid ($H_3PO_4$) in a manner such that the two components may be blended into a uniform slurry or paste. The composition of the reagent of this invention is critical and exists within a narrow range. The phosphoric acid component used may be in a concentration range of from about 75% to about 117% (about 54% to about 85% $P_4O_{10}$) and is conveniently available commercially in the range of from about 85% to about 115%. The phosphoric anhydride component used is of high purity and essentially anhydrous. The narrow phosphation reagent composition range is from about 118% to about 125% (expressed as an effective equivalent percent polyphosphoric acid) preferably from about 119%–124% and most preferably from about 121%–123%.

Neither the time nor the temperature of the process for the manufacture of the phosphation reagent is critical. The time may range from the minimum required to obtain a uniform mixture in which the $P_4O_{10}$ powder is thoroughly wetted by and blended with the phosphoric acid. The order of addition is not critical and can be adapted to the available equipment.

The initial temperature may begin at ambient room temperature and range to 180° C. as dictated by temperature control, stirring and pumping capabilities of the reactor and associated equipment. However, prolonged periods at elevated temperatures should be avoided.

The phosphation reagent is stable to storage under reasonable conditions as long as anhydrous conditions are maintained in the storage container. Like all condensed (dehydrated) phosphoric acid materials, the phosphation reagent is hygroscopic and absorption of air moisture will result in a change in the composition.

With respect to the use of the phosphation reagent in a phosphation esterification reaction, the alcohol may be added to the phosphation reagent or the reagent may be added to the alcohol within the mixing and temperature constraints of the reactor in accordance with standard practices well known in the art. It is not necessary to stage the reaction. Simple combination of the organic alcohol and the phosphation reagent in the proper stoichiometric molar ratio of four alcohols per equivalent mole of $P_4O_{10}$, i.e. equimolar alcohol-phosphorus, is all that is required. A moderate excess of alcohol does not significantly change the MAP-:DAP ratio and will contribute to a higher residual alcohol content in the final ester product. Use of significantly less than the stoichiometric amount of alcohol retards the dissolution rate and leaves an undesirably high level of pyrophosphate intermediates which would have to be converted by addition of additional alcohol and/or water.

The organic hydroxy compounds which can be phosphated by the phosphation reagent of this invention are of the formula $RO\{C_nH_{2n}O\}_xH$ wherein R is selected from the group consisting of a saturated or unsaturated aliphatic $C_1$–$C_{30}$ straight or branched carbon chain, a phenyl, a mono-,di-,or tri-substituted phenyl, a phenyl $C_1$–$C_6$ alkyl and a mono-,di-,or tri-substituted phenyl $C_1$–$C_6$ alkyl, wherein the phenyl substituent group(s) each have a total of 1 to 30 carbon atoms, and wherein each substitution can be a saturated or unsaturated straight or branched carbon chain, a phenyl, an alkyl phenyl, a phenyl alkyl, or an alkyl phenyl alkyl group; wherein n is from 2 to 4 and may be the same or different for each alkylene oxide unit; and wherein x if from 0 to 100.

Examples of preferred alcohols are lauryl, myristol and cetyl alcohols and their ethoxylates; blends thereof; and tristyryl phenol ethoxylates.

As noted above, the times and temperatures required for reacting the phosphation reagent with the alcohol can be easily determined by those skilled in the art and are principally a function of the mixing, pumping, and temperature control capabilities of the reactor and associated equipment. During the initial blending step, preferably, the initial temperature would be high enough to promote easy mixing and dissolution, i.e. from about ambient room temperature to about 80° C., but could be the same as the cook temperature. Similarly, the cook temperature would be dictated by the need to obtain reasonably short cycle times without excessive discoloration of the product; typically from about 75° C. to about 100° C. Typical reaction times are from about greater than 3 to about 12 hours. Times from about 4 to about 7 hours are preferred, however, depending upon temperature, to prevent product degradation and color formation.

During the reaction process, a point is reached at which the principal remaining phosphate intermediates are the relatively unreactive pyrophosphates, which together with the alcohol are at low concentration. Since little additional beneficial change in the composition can be achieved by prolonged heating, it is expedient to add a small amount of water to complete the conversion of the pyrophosphates to orthophosphates. Upon completion of this step, the liquor is customarily cooled slightly and hydrogen peroxide is added to reduce the color.

The characteristics of the above processes for the formation of the phosphation reagent and its reaction with an alcohol to produce a phosphate ester product mixture, suggest that both processes would be adaptable to continuous processes run either concurrently or consecutively.

The present invention will be explained in more detail with reference to the following non-limiting working examples.

EXAMPLE 1

Preparation of Phosphation Reagent

A 2000 ml, four-necked, round bottomed flask was fitted with an inert, dry gas inlet (12' 18 ga. stainless steel needle) and outlet through an Allihn condenser connected to a silicone fluid bubbler tube, an overhead motor driven teflon paddle stirrer, thermometer, and pressure equalizing, screw-feed powder addition funnel. The oven dried apparatus was assembled and heated above 100° C. for an hour with a positive argon gas flow to remove residual traces of moisture, then allowed to cool.

The flask was quickly charged with 190.5 g 105% phosphoric acid (Rhône-Poulenc Super Phos 105™) and the funnel with 218.9 g $P_4O_{10}$, against a positive, dry argon gas flow. The $P_4O_{10}$ was sifted into the gently stirred acid over a 42 minute period with occasional use of an 18° C. water bath to maintain the temperature in the flask at 30–35° C. Only 217.6 g $P_4O_{10}$ was actually transferred to the flask. When the $P_4O_{10}$ powder had been evenly dispersed in the viscous, white slurry, the water bath was replaced by an oil bath which was heated to 100° C. over a 53 minute period. After 10 additional minutes, during which time the mixture reached a maximum temperature of 88° C., the bath was lowered and the relatively easily stirred, uniform slurry was allowed to cool. The average composition was calculated to be 122.7% polyphosphoric acid (88.84% $P_4O_{10}$).

EXAMPLE 2

Phosphation of Lauryl Alcohol

To 388.2 g of the phosphation reagent mixture in the flask in Example 1 was quickly added 911.7 g lauryl alcohol against a positive flow of argon gas. The mixture was warmed to 80° C. with slow stirring at first, because of the high room temperature viscosity of the phosphation reagent. The stirring speed was increased as the mixture warmed and the solids dispersed. After the solids had dissolved, the temperature was increased to 87° C. and maintained for 290 minutes. Deionized water, (8.0 g), was then added to hydrolyze the residual pyrophosphate intermediates and after 30 minutes, during which time the temperature was allowed to drop to 78° C., 5.0 g of 15% hydrogen peroxide was added. The temperature and agitation were maintained for an additional 30 minutes, and the clear, nearly colorless liquor was cooled to 70° C. and bottled.

The residual alcohol content was determined to be 1.8 mole percent from the proton nuclear magnetic resonance signal ratios between the hydroxy and phosphate substituted methylene groups. The phosphate molar ratios, determined from quantitative phosphorus -31 nuclear magnetic resonance data, were 0.122 phosphoric acid, 0.776 monolauryl phosphate and 0.102 dilauryl phosphate. Conversion to weight percent gave 1.3% nonionic (residual alcohol), 4.6% phosphoric acid, 77.5% monolauryl phosphate and 16.7% dilauryl phosphate, for a MAP:DAP weight ratio of 82.3:17.7.

EXAMPLES 3–7

To determine the effect of aging temperature upon the performance of the phosphation reagent, a series of experiments was run in which the aging time and temperature for the homogenization and equilibration of the phosphating species in the reagent was varied. For convenience and better efficiency on the lab scale, the 105% phosphoric acid was added to the $P_4O_{10}$.

Accordingly, the apparatus in Examples 1 and 2 was assembled and dried, except that a 1000 mnl flask was used and the powder addition funnel was replaced with a simple, pressure equalizing, liquid addition funnel. The funnel was charged with 110.9 g Super Phos 105™ polyphosphoric acid and the flask with 126.3 g $P_4O_{10}$. The room temperature (21° C.) acid was run into the stirred powder over a 10 minute period. Stirring was continued and the slurry temperature was allowed to rise to a maximum of 55° C. within 5 minutes after the addition to keep the viscosity low enough to wet out the powder evenly. After 5 minutes, the oil bath was raised, heated to 100° C. in 15 minutes and maintained for an additional two hours before being lowered to mark the end of the aging period. The slurry was allowed to cool naturally to 23° C., at which point it was barely stirrable (only a few rpm). Lauryl alcohol, 524.1 g, was quickly added. The mixture was heated to 80° C. with a brief overshoot to 92° (heat of reaction) and back within 20 minutes. A temperature of 78–82° C. was maintained for five hours after the solids had dissolved, 3.8 g deionized water was added and, after two more hours at 82° C., the clear liquid was cooled slightly and bottled warm before it solidified.

Analysis showed the phosphate molar ratios to be 0.157 phosphoric acid, 0.746 monolauryl phosphate, and 0.097 dilauryl phosphate. The residual alcohol (percent nonionics) was determined by a standard ion exchange resin method to be 2.3 weight percent, allowing calculation of the remaining components to be 5.9% phosphoric acid, 75.8% monolauryl phosphate, and 16.0% dilauryl phosphate with a MAP:DAP weight ratio of 82.5:17.5.

Similar experiments were run in which the aging time was varied from over two hours to essentially none. In the latter case, the alcohol was added 13 minutes after the acid and $P_4O_{10}$ had been combined, to allow only for the temperature excursion from the heat of reaction to peak at 68° C. and the $P_4O_{10}$ powder to be wetted and blended into the slurry. Oil bath temperatures for all but the above special example in this series, were varied from 60 to 220° C. in 40° increments. The 220° bath aging period produced a hard, discolored material which was not readily soluble in the alcohol so the experiment was not worked up. The results in Table 1 show that phosphate compositions which exceed the 80:20 weight ratio are produced by the phosphation reagent under all of the times and temperatures evaluated except the latter, high temperature (220° C.) extreme.

Because of equipment limitations, the process variation in which the acid and $P_4O_{10}$ powder were combined, homogenized and pumped directly into the alcohol at 60°–80°, reaction temperature could not be effectively evaluated. These data strongly suggest, however, that similar results would be obtained. For instance, use of a reactive extrusion process which metered the acid into the $P_4O_{10}$ powder at one of the early flights of a twin screw extruder (or other screw design to provide homogenization, or followed by a static bow-tie mixing line) then extruded the phosphation agent as filaments into the stirred alcohol for rapid dissolution, should minimize the reaction time yet still have ample provision for control. Such an approach should be adaptable to a continuous process mode of operation.

EXAMPLES 8–10

The apparatus setup and procedures utilized in the balance of the Examples are those used in Examples 3–7 except as indicated. The effect of the concentration of the phosphoric acid used to prepare the phosphation reagent was determined in the next series, also reported in Table 1, in which aging periods were again varied and both orders of addition were used. The results show that the entire commonly available commercial range of phosphoric acid, from 85 to 115%, can be used to prepare a phosphation reagent which consistently produces a product with a MAP:DAP weight ratio above 80:20, combined with a low level of unreacted alcohol and phosphoric acid.

EXAMPLE 11

In an attempt to further reduce the phosphoric acid level in the final product mixture, a higher molar ratio of alcohol to $P_4O_{10}$ was evaluated. .

In the apparatus described in Example 3, the 1000 ml flask was charged with 97.8 g $P_4O_{10}$ under a positive flow of dry argon and 86.5 g Super Phos 105™ was added at ambient, 23° C., temperature to the gently stirring powder over a 35 minute period. The temperature reached a maximum of 60° at 20 minutes with about 60% of the acid added. The remainder of the acid converted the wetted, clumpy mixture into a smooth, white, fudge-like substance. The viscosity increased as the temperature returned to ambient, so the stirring rate was reduced to about 8 rpm. As the mixture was reheated to the 100° C. (oil bath) aging temperature, the viscosity decreased again, as expected. At 22° C., the material was still stirrable, but with difficulty. Heating to 28° C. significantly improved the stirring efficiency and by 42° C., the material was again conveniently stirrable at 25 rpm. The phosphation reagent was continuously stirred for two hours in the bath at 100° with relatively little change; then allowed to cool.

With the phosphation reagent at 36° C., (oil bath 50°), 496.2 g lauryl alcohol was added in about two minutes. This gave a molar ratio of alcohol to total phosphorus, expressed as $P_4O_{10}$, of 4.75:1.00 (1.19 mole alcohol per mole phosphorus). The liquor temperature of the easily stirred mixture leveled off at the 50° C. bath temperature in 15 minutes without overshooting, so it was warmed to 80° C. where the temperature and stirring were maintained for nine hours. Deionized water (3.5 g) was added; 80–82° C. was maintained for two additional hours; the mixture cooled; and then bottled before solidification.

The phosphate molar ratios were 0.116 phosphoric acid, 0.783 monolauryl phosphate and 0.101 dilauryl phosphate. The residual alcohol determined as percent-nonionics was 16.8% with the weight percent of the phosphates then calculated to be 3.6% phosphoric acid, 65.7% monolauryl phosphate and 13.9% dilauryl phosphate for a MAP:DAP ratio of 82.5:17.5. A slight decrease, therefore, was observed in the phosphoric acid, the MAP:DAP ratio was not affected, and the excess alcohol essentially remained as a nonionic diluent.

EXAMPLES 12–16

The results in Table 1 for Examples 12–16, inclusive, demonstrate that the critical variable is the composition of the phosphation reagent itself. In this series, the reagent was prepared by addition of the Super Phos 105™ to the phosphoric anhydride.

The range evaluated essentially defines the surprisingly narrow range required to produce the desired ester compositions. The upper limit of the concentration also approached the practical limit from the standpoint of reagent transfer. In contrast to the simplicity and convenience of the 122.6% composition in Example 11, the viscosity of the 125% phosphation reagent of Example 13 was so high that an oil bath temperature of 140° was required to maintain good stirring within the limitations of the laboratory apparatus during the curing period. The phosphation reagent dissolution rate was also significantly slower. The 127% phosphation reagent composition did not blend into a smooth, uniform mixture, but rather agglomerated into wet clumps which could be moved by the stirrer blade but not stirred efficiently. A 100° C. oil bath curing temperature was used, but it effected little apparent change on this high $P_4O_{10}$ content reagent.

The lower levels of the reagent, i.e. 119.9% and 115.1% were prepared and used without complication.

The results show, as expected, an increase in the MAP:DAP ratio, as the composition shifts from phosphoric anhydride rich to polyphosphoric acid rich. The 70:30 MAP:DAP ratio produced by the 125% composition is the lower limit of the product mixtures shown to have useful foaming and solubility properties (H. Mori et al. U.S. Pat. No. 5,254,691, Oct. 19, 1993) and considering other process factors such as viscosity and dissolution rates, defines the upper limit of the desirable composition range. The results for the 127% composition show it to be beyond the desirable composition range.

The MAP:DAP ratio produced by the 119.9% composition was in the favorable range established by the earlier examples, but the residual phosphoric acid and alcohol levels both increased noticeably. These trends were more pronounced for the 115% composition, Example 15. A control experiment in which 115% polyphosphoric acid was used directly for the phosphation, Example 16, produced similar results showing the phosphation-reagent composition and process offers no advantage at that concentration. The upper limit of commercial processes in which polyphosphoric acid is produced by orthophosphoric acid dehydration is about 117.5% because of the excessively high viscosities resulting from the long anhydride polymer chains. The lower viscosities of even the higher strength phosphation reagents of this invention are much more easily handled in a commercial process. Since the phosphation reagent performs as though it were a polyphosphoric acid at the 115% concentration, it would be expected to provide a continuum of compositions with its pragmatic lower limit being that at which use of commercially available polyphosphoric acid becomes impractical, about 117–118%.

Comparative Example 1

Two Step Process

Reaction of Lauryl Alcohol with Polyphosphoric Acid Prior to Phosphoric Anhydride Addition In a 1 l flask equipped similarly to Example 1, 81.1 g 105% phosphoric acid (0.430 mole phosphoric acid, 0.179 mole pyrophosphoric acid and 0.027 mole tripolyphosphoric acid) and 37.0 g dodecyl (lauryl) alcohol (0.20 mole) were combined at room temperature. The temperature of the stirred solution rose to a maximum of 35° C. in 10 minutes and the mixture changed to a whipped cream consistency. It was stiff enough to retain its shape if stirring were stopped, yet was easily stirrable. Heat was applied to raise the temperature to 72° C. within two hours and held for an additional 14 hours. The phosphate composition by $^{31}$P NMR analysis of the viscous, creamy mass was 0.600 mole phosphoric acid, 0.179 mole monolauryl phosphate, and 0.045 mole pyrophosphoric acid, verifying substantial conversion of the polyphosphoric acid components and absence of dialkyl phosphate.

To the 98.0 g which remained after sampling (83.0% of the above mixture), 302.6 g of lauryl alcohol (1.624 mole) was added and the liquor heated to 52° C. to dissolve the phosphate mixture heel. The solution thus containing phosphoric acid and the alcohol phosphate was cooled to 30° C. and 74.9 g phosphoric anhydride was added in nearly equal portions, 25 minutes apart. The powder dispersed readily to produce a white, creamy, easily stirrable slurry with the temperature rising from 41° C. at the end of the addition to a maximum of 61° C. 10 minutes later. The temperature was raised to 80° C. and maintained for 18 hours, 2.4 g deionized water was added, the mixture stirred at 80° C. for two hours, cooled to 60° C. and bottled.

The total raw materials charged were 1.788 mole lauryl alcohol (0.164 mole in heel, 1.624 in step two), 0.719 mole phosphorus (as 105% polyphosphoric acid), and 0.264 mole phosphoric anhydride (1.055 mole phosphorus). The calculated phosphation reagent average composition was 122.7% polyphosphoric acid, and the molar ratio of alcohol to phosphorus was 1.008:1.000. The product phosphate molar ratios were 0.146 phosphoric acid, 0.730 monolauryl phosphate and 0.124 dilauryl phosphate. The weight composition was 1.0% nonionics, 5.4% phosphoric acid, 73.3% lauryl phosphate and 20.3% dilauryl phosphate, with a MAP:DAP ratio of 78.3:21.7. This composition is below the 80:20 ratio regarded as the minimum for a desirable monoalkyl phosphate composition and further below the 85:15 ratio obtained by the process modification of this invention, even though the amount of lauryl phosphate produced in the first step consumed only about 10% of the total alcohol and phosphation reagent charge and contained no dialkyl phosphate coproduct.

The process of the instant invention is decidedly superior to the published Comparative Example 1. in U.S. Pat. No. 4,350,645, in which the phosphoric anhydride apparently was not added entirely under controlled, lower temperature conditions to minimize direct reaction between the phosphoric anhydride and alcohol. The high amount of dialkyl phosphate characteristic of that reaction is reflected in the final product molar composition, which was 0.149 phosphoric acid, 0.662 monolauryl phosphate and 0.189 dilauryl phosphate (conversion of MAP:DAP molar ratio to weight ratio gives 68.2:31.8) even though the overall reagent ratios are an average composition of 122.5% polyphosphoric acid equivalent for the phosphation reagent and the alcohol to phosphorus molar ratio is 1.00:1.00.

Comparative Examples 2 and 3

The following experiments were conducted with regard to Japanese Patent Publication 42-6730.

Comparative to Example 1 of 42-6730

To a predried assembly consisting of a 500 ml round bottomed flask equipped as in Example 1 of this application was charged 186.31 g dodecyl alcohol against a positive flow of argon gas. Phosphoric acid, 85%, was charged to the pressure equalizing addition funnel and 23.40 g was added to the stirred, preheated alcohol over an 11 minute period with the temperature being maintained at 42–44° C. The liquor temperature was allowed to drop naturally 38° C. over seven minutes and maintained at 35–38° C. for two hours with continued stirring. The liquid addition funnel was replaced by an airtight, screw-feed, pressure-equalizing powder addition funnel containing phosphoric anhydride during this period. A water bath was raised to the flask and 56.72 g phosphoric anhydride was added with stirring over a 131 minute interval with the temperature at 38–39° C. The liquor temperature was raised to 60° C. in 35 minutes and maintained at 63–64° C. for most of the three hour post addition cook period. The liquor was allowed to cool to 58° C. during a four minute interval during which a 22.18 g sample was removed.

The liquor was then diluted with 224.54 g anhydrous ethanol and transferred quantitatively to a 3000 ml flask with five washings of anhydrous ethanol; total ethanol diluent weight was 1215.23 g. The solution was heated to reflux in accord with the work up procedure described in the body of 42-6730. A portion of the solution was removed and the ethanol removed under vacuum.

Analysis of the first sample, taken after completion of the process claimed in 42-6730, by quantitative C-13 nuclear magnetic resonance spectroscopy showed the integral ratio between the residual alcohol and the combined alkyl phosphate alpha-carbon signals to be 7.3:92.7, the total integral of these groups matching the value for the terminal methyl group and well resolved individual, internal methylene signals. The P-31 nuclear magnetic resonance spectrum showed the mixture to still contain 13.8 mole percent pyrophosphate intermediates. In view of the 7.3 mole percent unreacted alcohol, and the 13.8 mole percent residual pyrophosphates, it would be impossible to achieve the 94.7% yield of monododecyl phosphate ester as reported by the Japanese Patent Publication 42-6730 without further reaction.

Analysis of the mixture concentrated after the ethanol work-up showed the amount of pyrophosphate intermediates to have been reduced to about 6.8 mole percent, with an approximately even split between the alkyl and non-alkylated groups. The monoalkyl and dialkyl signal regions now both contained overlapping signals, indicating the formation of ethyl as well as dodecyl substituted phosphates; i.e., some of the dialkyl phosphates could contain both an ethyl and dodecyl group and monoethyl phosphate was produced.

The C-13 spectrum similarly confirmed formation of ethyl phosphate species, but at an approximately 12:88 mole ratio to the dodecyl phosphate signals. This ratio of about double that expected from reaction with the portion of the pyrophosphates which were consumed, was explained by the 5 mole percent increase in the residual dodecyl alcohol, to 12.3%. Apparently, a small amount of transesterification had occurred.

In a separate experiment, the absence of alkyl phosphates in the dodecyl alcohol—85% phosphoric acid solution after the first "reaction" period (i.e. only orthophosphoric acid was present) was confirmed. Additionally, the two portions of the product mixture purified by separation of the precipitated product from the ethanol soluble product were analyzed. The P-31 spectrum of the filter cake showed molar ratios of 8.6% phosphoric acid, 53.5% monoalkyl phosphates and 37.9% dialkyl phosphates. The solid obtained by evaporation of the ethanol from the filtrate was 15.5% phosphoric acid, 77.5% monoalkyl phosphates and 7.0% dialkyl phosphates. An efficient separation was therefore not achieved in the purification step; monododecyl phosphate was removed in the filter cake and didodecyl phosphate was carried over into the ethanol solution.

Comparative to Example 2 OF 42-6730

To a 500 ml flask equipped as in the above comparative example, was added 195.06 g 2-ethylhexyl alcohol under argon. The liquor was warmed to 70° C. and the addition of 85% phosphoric acid was initiated. After 18 minutes, the addition was stopped, for a total of 28.88 g, with the temperature having risen to 73° C. Samples of 10.09 g and 9.74 g were removed after 12 and 77 minutes, the temperature being maintained at 72–73° C. The P-31 NMR spectrum confirmed that only phosphoric acid was present in both cases; no reaction with alcohol to form esters had occurred.

The solution was cooled to 41° C. and, correcting for the mass removed as samples, 96.73 g phosphoric anhydride was added over a 98 minute period during which the temperature was allowed to rise gradually to 47° C. The reaction was continued at the "same temperature" for 30 minutes, as stated in the 42-6730 example (actually, the temperature rose to 48° C). Since the mixture was still cloudy with some clumps of phosphoric anhydride remaining, 25.55 g was removed for analysis. The molar ratios of the signals in the orthophosphate (ca. −13 ppm) to higher polyphosphate (ca. −27 ppm) regions were 23.7: 64.7: 11.6, indicating limited conversion. The liquor was, therefore, heated over the next hour to 70° C. to begin a second 30 minute reaction period now at 70–79° C., assuming "same temperature" meant as was used for the phosphoric acid "reaction" period. Analysis of a fresh 25.87 g sample of the mixture after this period showed the ratios between signals in the orthophosphate, pyrophosphate and polyphosphate regions to be 40.4:55.4:4.2, still indicative of very incomplete conversion.

The remaining liquor was diluted with 230.60 g anhydrous ethanol and washed into a 2000 ml flask with three volumes of fresh ethanol for a total of 1251.03 g diluent. The solution was then heated to reflux, heating continued for 20 minutes, then the liquor was allowed to cool naturally in the oil bath and sampled. The clear solution was refrigerated at +10° C. and checked periodically for crystal formation. None was observed over a seven day period, so the work-up was discontinued.

The P-31 spectrum of the final sample, after concentration, showed it to still contain a significant proportion of pyrophosphate intermediates in molar ratio of 32.0:68.0 to the orthophosphates. The pyrophosphate six-signal pattern was essentially the same as that observed from the sample taken prior to the ethanol treatment indicating the only change had been conversion of a portion of the pyrophosphates to orthophosphates. The two orthophosphate ester peaks (mono and dialkyl) now both had smaller side peaks showing the presence of the ethyl as well as the 2-ethylhexyl groups of each product.

The C-13 NMR spectrum confirmed the formation of the ethyl substituted as well as 2-ethylhexyl substituted mono- and dialkyl phosphates. The mole ratio of ethyl to 2-ethylhexyl phosphate groups was 21:79.

Although the amount of the various phosphorus species would be difficult to calculate from the final spectra because of the overlap of the ethyl and 2-ethylhexyl signals, an estimate of a final composition which would have been produced from the pre-ethanol treated mixture can be calculated if one were to assume that the pyro and tripolyphosphate intermediates were converted to orthophosphates only by reaction with 2-ethylhexyl alcohol and no transesterification occurred. (In this example, such conversion would not have occurred because the phosphation reagent was in excess!). The mole percentages of the thus estimated composition would be 12.6% phosphoric acid, 63.9% mono(2-ethylhexyl) phosphate and 23.6% di(2-ethylhexyl) phosphate. Conversion to normalized weight percentages (values would be lower if residual alcohol were present) would be 5.5 weight percent phosphoric acid, 60.3 weight percent mono-(2-ethylhexyl) phosphate and 34.2% di(2-ethylhexyl) phosphate.

The above data show that the claimed procedure was not sufficient to complete the conversion of either the alcohol or phosphorus reagents to orthophosphates. No formation of alkyl phosphates occurred in the first stage reaction of 85% phosphoric acid with the alcohol and completion of the reaction after the phosphoric anhydride addition required the work up procedure involving dissolution in a large excess of ethanol and yet another additional, undefined heating period.

In both examples, the product mixtures before and even after the second stage reaction with ethanol, produced mixtures containing such high levels of residual starting alcohol, residual phosphoric acid and/or dialkyl phosphate that the 94.7 and 90.2% yields of monoalkyl phosphate reported were not present at anytime during the process.

Finally, the second example using a phosphation reagent composition effectively equivalent to 125.9 weight percent polyphosphoric acid, approaching the upper end of the 91.4 to 126.8% range described in the 42-6730 case, was beyond the 125% maximnum useful concentration defined herein and, as expected, produced a weight ratio lower than the 70:30 monoalkyl dialkyl phosphate defined as functionally, but marginally acceptable in performance. (See Examples 12 and 13 in copending U.S. Ser. No. 08/220,069 filed Mar. 30, 1994).

TABLE 1

PHOSPHATION REAGENT COMPOSITIONS, CONDITIONS AND PRODUCT COMPOSITIONS

| EXAMPLE NUMBERS | COMPOSITION (Wt. % $H_3PO_4$) | AGING PERIOD Mins. @ T (° C.) | | ALCOHOL:$P_4O_{10}$ MOLAR RATIO | ADDITION MODE[a] | INITIAL $H_3PO_4$ CONC. (WT. %) |
|---|---|---|---|---|---|---|
| 1 & 2 | 122.7 | 10 | 100° | 4.028 | P-L | 105 |
| 3 | 122.9 | 60 | 60° | 3.999 | L-P | 105 |
| 4 | 122.7 | 120 | 100° | 4.000 | L-P | 105 |
| 5 | 122.5 | 130 | 140° | 4.000 | L-P | 105 |
| 6 | 122.8 | 120 | 180° | 3.985 | L-P | 105 |
| 7 | 122.5 | None | | 3.979 | P-L | 105 |
| 8 | 122.3 | 60 | 100° | 4.040 | P-L | 85 |
| 9 | 122.6 | 70 | 100° | 4.010 | P-L | 100 |
| 10 | 122.7 | 120 | 100° | 3.999 | L-P | 115 |
| 11 | 122.6 | 190 | 100° | 4.748 | L-P | 105 |
| 12 | 127.1 | 120 | 100° | 3.991 | L-P | 105 |
| 13 | 125.0 | 110 | 140° | 3.999 | L-P | 105 |
| 14 | 119.9 | 120 | 140° | 3.998 | L-P | 105 |
| 15 | 115.1 | 120 | 100° | 3.994 | L-P | 105 |
| 16 | 115.0 | — | — | 3.998 | — | 115 |

| EXAMPLE NUMBERS | PHOSPHATE MOLAR RATIOS[b] | | | PRODUCT COMPOSITION[b] (WT. %) | | | | MAP:DAP (WT.:WT.) |
|---|---|---|---|---|---|---|---|---|
| | PA | MAP | DAP | N.I. | PA | MAP | DAP | |
| 1 & 2 | 0.122 | 0.776 | 0.102 | 1.3 | 4.6 | 77.5 | 16.7 | 82.3:17.7 |
| 3 | 0.126 | 0.764 | 0.109 | 1.9 | 4.6 | 75.8 | 17.7 | 81.1:18.9 |
| 4 | 0.157 | 0.746 | 0.097 | 2.3 | 5.9 | 75.8 | 16.0 | 82.5:17.5 |
| 5 | 0.142 | 0.787 | 0.072 | 2.0 | 5.3 | 80.7 | 12.0 | 87.1:12.9 |
| 6 | 0.159 | 0.758 | 0.083 | 3.2 | 6.0 | 77.0 | 13.8 | 84.8:15.2 |
| 7 | 0.137 | 0.763 | 0.099 | 1.2 | 5.1 | 77.3 | 16.3 | 82.6:17.4 |
| 8 | 0.139 | 0.769 | 0.092 | 1.6 | 5.1 | 78.0 | 15.3 | 83.6:16.4 |
| 9 | 0.139 | 0.769 | 0.092 | 2.2 | 5.1 | 77.5 | 15.2 | 83.6:16.4 |
| 10 | 0.123 | 0.769 | 0.108 | 1.2 | 4.6 | 77.7 | 17.8 | 81.4:18.6 |
| 11 | 0.116 | 0.783 | 0.101 | 16.8 | 3.6 | 65.7 | 13.9 | 82.5:17.5 |
| 12 | 0.249 | 0.532 | 0.220 | 2.7 | 9.1 | 52.7 | 35.5 | 59.7:40.3 |
| 13 | 0.174 | 0.652 | 0.175 | 1.0 | 6.3 | 64.5 | 28.2 | 69.6:30.4 |
| 14 | 0.185 | 0.741 | 0.074 | 5.0 | 7.0 | 75.7 | 12.4 | 86.0:14.0 |
| 15 | 0.302 | 0.671 | 0.028 | 15.1 | 11.4 | 68.9 | 4.6 | 93.7:6.3 |
| 16 | 0.282 | 0.689 | 0.029 | 14.8 | 10.5 | 69.9 | 4.8 | 93.6:6.4 |

[a]P-L means Powder ($P_4O_{10}$) is added to liquid ($H_3PO_4$); (L-P means liquid to powder).
[b]Phosphoric acid (PA), monoalkyl phosphate (MAP), dialkyl phosphate (DAP) and nonionic (N.I.)

Having set forth the general nature and some examples of the present invention, the embodiments in which an exclusive property or privilege is claimed are defined as follows:

1. A composition produced by intimately mixing and exclusively reacting an effective amount of phosphoric anhydride with from about 75 weight % to about 117 weight % polyphosphoric acid (54 weight % to 85 weight % $P_4O_{10}$) to produce a uniform slurry or paste having an effective equivalent polyphosphoric acid weight percent of from about 118 to 125.

2. The composition of claim 1 wherein the effective equivalent weight percent of polyphosphoric acid is from about 119 to 124.

3. The composition of claim 1 wherein the effective equivalent weight percent of polyphosphoric acid is from about 121 to 123.

* * * * *